(12) United States Patent
den Hoed

(10) Patent No.: US 10,752,671 B2
(45) Date of Patent: Aug. 25, 2020

(54) METHOD OF MAKING COLLAGEN POWDER FROM MARINE CARTILAGE AND SKIN

(71) Applicant: Robert den Hoed, Sioux Center, IA (US)

(72) Inventor: Robert den Hoed, Sioux Center, IA (US)

(73) Assignee: Robert den Hoed, Sioux Center, IA (US)

( * ) Notice: Subject to any disclaimer, the term of this patent is extended or adjusted under 35 U.S.C. 154(b) by 491 days.

(21) Appl. No.: 15/234,712

(22) Filed: Aug. 11, 2016

(65) Prior Publication Data

US 2016/0347820 A1  Dec. 1, 2016

Related U.S. Application Data

(62) Division of application No. 14/623,718, filed on Feb. 17, 2015, now abandoned, which is a division of application No. 14/157,609, filed on Jan. 17, 2014.

(51) Int. Cl.
*C07K 14/78* (2006.01)
*C12P 21/06* (2006.01)

(52) U.S. Cl.
CPC .............. *C07K 14/78* (2013.01); *C12P 21/06* (2013.01)

(58) Field of Classification Search
None
See application file for complete search history.

(56) References Cited

U.S. PATENT DOCUMENTS

| | | | |
|---|---|---|---|
| 5,093,474 A * | 3/1992 | Grossman | C09H 3/00 426/576 |
| 6,780,841 B2 | 8/2004 | Ishaq | |
| 2002/0182290 A1 | 12/2002 | Nielsen | |
| 2007/0004629 A1 | 1/2007 | Stiles et al. | |
| 2013/0035473 A1 | 2/2013 | Summers et al. | |

OTHER PUBLICATIONS

Potaros et al., Characteristics of Collagen from Nile Tilapia (*Oreochromis niloticus*) Skin Isolated by Two Different Methods, Kasetsart J. (Nat. Sci.), vol. 43: pp. 584-593, 2009.*
Aguirre-Alvarez et al., CyTA-Journal of Food, vol. 9, No. 3, Nov. 2011, pp. 243-249.*
Brier et al., FEBS Journal, vol. 274 (2007), pp. 6152-6166.*
Feng et al., Pharmacogn Mag. Oct.-Dec. 2013; 9 (Suppl 1):S32-S37.*
Kittiphattanabawon, Food Chemistry 89 (2005), pp. 363-372.*
Kittiphattanabawon, Food Chemistry 119 (2010), pp. 1519-1526.*
Pall Seitz K Series Depth Filter Sheets, Aug. 2011, retrieved from the internet: https://food-beverage.pall.com/content/dam/pall/food-beverage/literature-library/non-gated/FBKEN.pdf.*

* cited by examiner

*Primary Examiner* — Scott Long
*Assistant Examiner* — Evelyn Y Pyla
(74) *Attorney, Agent, or Firm* — Zarley Law Firm, P.L.C.

(57) ABSTRACT

A method of making hydrolyzed marine Type II collagen includes the mixing of marine cartilage, water, an enzyme and a protease enzyme for an extended period of time. Once mixed, the mixture is heated for a period of time at 150° F. Once heated, the enzymes are deactivated, the bone sediment separated, and the fat removed. Next, maltodextrin is added to the mixture and finally the mixture is spray dried to form a collagen powder.

12 Claims, 4 Drawing Sheets

METHOD OF MAKING COLLAGEN POWDER FROM MARINE CARTILAGE AND SKIN

CROSS REFERENCE TO RELATED APPLICATION

This divisional application claims the benefit of U.S. Ser. No. 14/623,718 filed Feb. 17, 2015 which is a divisional that claims the benefit of U.S. Ser. No. 14/157,609 filed Jan. 17, 2014.

BACKGROUND OF THE INVENTION

This invention is directed to a method of making collagen powder. More particularly, this invention is directed to a method of making hydrolyzed Type II collagen from marine cartilage and hydrolyzed Type I collagen from marine skin.

Shark cartilage is no longer controversial throughout medical, allied medical or participant supportive treatment circles today. The main beneficial attributes that this substance delivers have been well established over the past number of years. The active combination of the elements responsible for triggering such beneficial action is still somewhat unknown.

Collagen is a fibrous protein that forms insoluble fibers of high tensile strength, which contains the unique amino acids hyroxyproline and hydrosylysine. It is rich in glycine, but lacks cysteine and tryptophan, and has an unusually regular amino-acid domain. It is a natural nontoxic substance that in prior studies showed positive beneficial results for treating degenerative diseases such as osteoarthritis and rheumatoid arthritis and other inflammatory diseases/conditions. It was also associated as a substance with cancer combating properties, research later backed up that claim. Collagen has been found to block a tumor's angiogenesis—the growth of new blood vessels that feed a tumor and help it grow.

Type II collagen is the principal component of extracellular matrix of articular/hyaline cartilage. It is composed of 15-25% of the wet weight, about half the dry weight and 90-95% of the total collagen content in the cartilage. Type II Collagen from shark cartilage induces a cytokine response in human leukocytes, but the main bio-active components remain somewhat elusive. Medical research tends to group all collagen together as unique but equal substances. Collagen can be difficult to digest and breakdown when taken orally. Because of this, it does not allow the release and breakdown of essential components that benefit the body.

An objective of the present invention is to provide a method of making collagen powder that raises a bodies pH levels from acid to more neutral range.

Another objective of the present invention is to provide a method of making a collagen powder consumed in capsule form to improve flexibility and reduce pain.

BRIEF SUMMARY OF THE INVENTION

A method of making hydrolyzed marine Type II collagen includes the mixing of marine cartilage, water, an enzyme and a protease enzyme for an extended period of time. Once mixed, the mixture is heated for a period of time at 150° F. Once heated, the enzymes are deactivated, the bone sediment separated, and the fat removed. Next, maltodextrin is added to the mixture and finally the mixture is spray dried to form a collagen powder.

DETAILED DESCRIPTION OF THE PREFERRED EMBODIMENT

Figure 1:
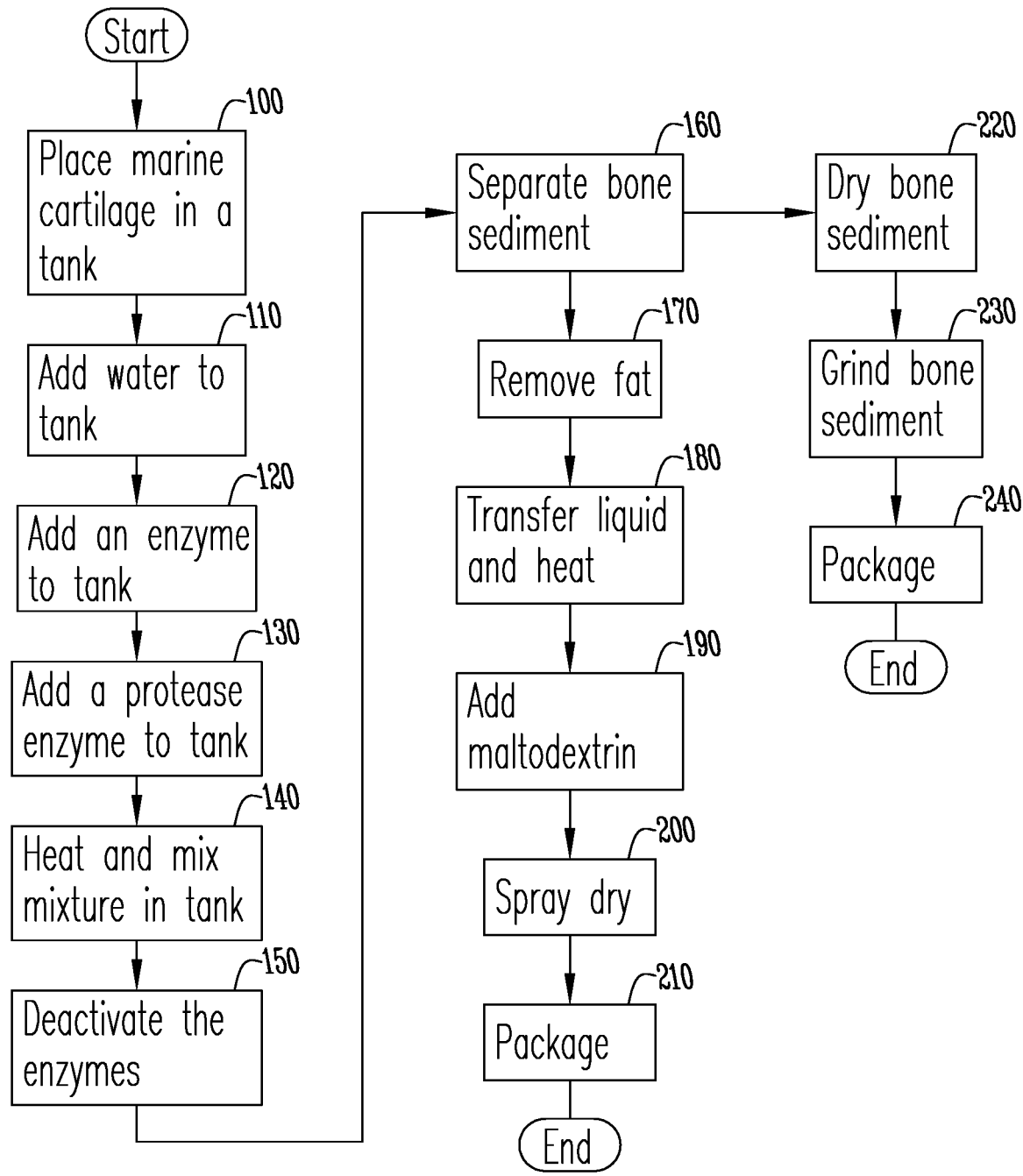
FIG. 1 is a flow diagram of a method of making collagen powder.
Figure 2:
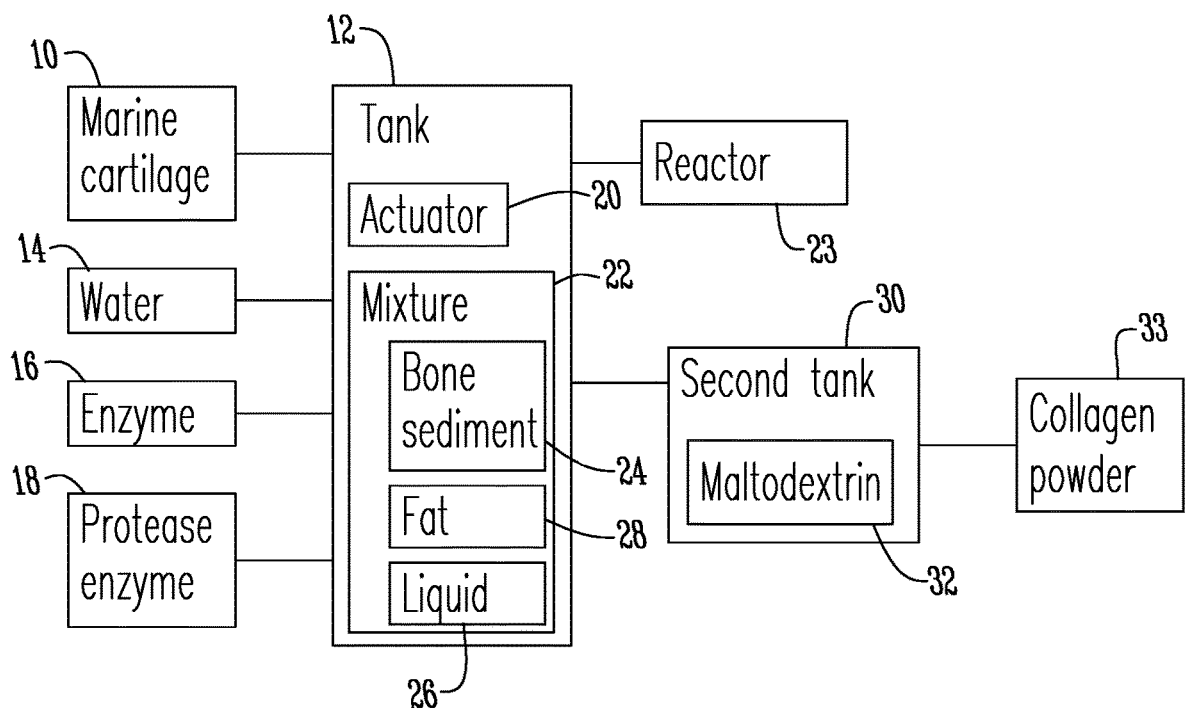
FIG. 2 is a schematic drawing of an environment for making collagen powder.
Figure 3:
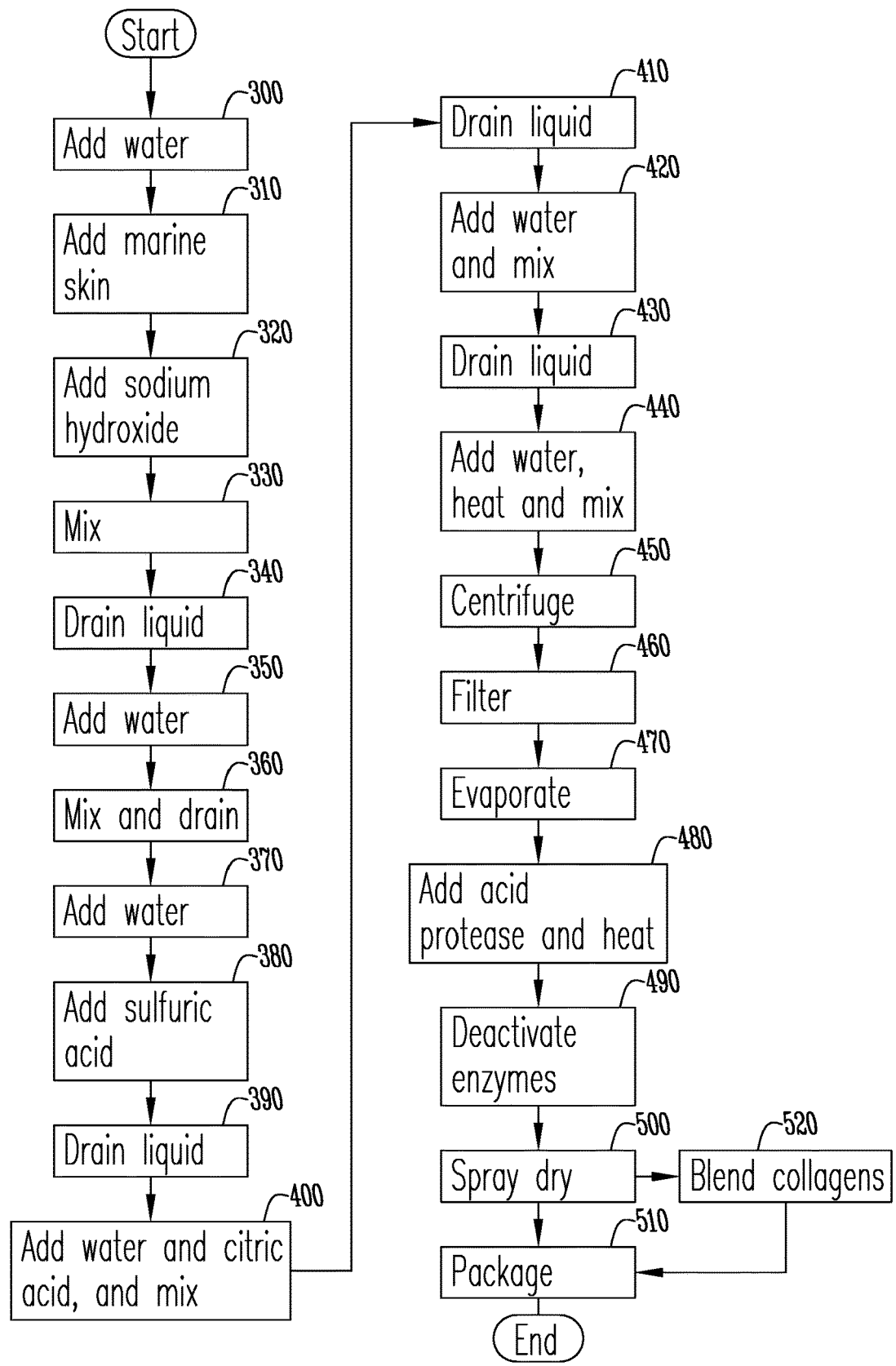
FIG. 3 is a flow diagram of a method of making collagen powder.
Figure 4:
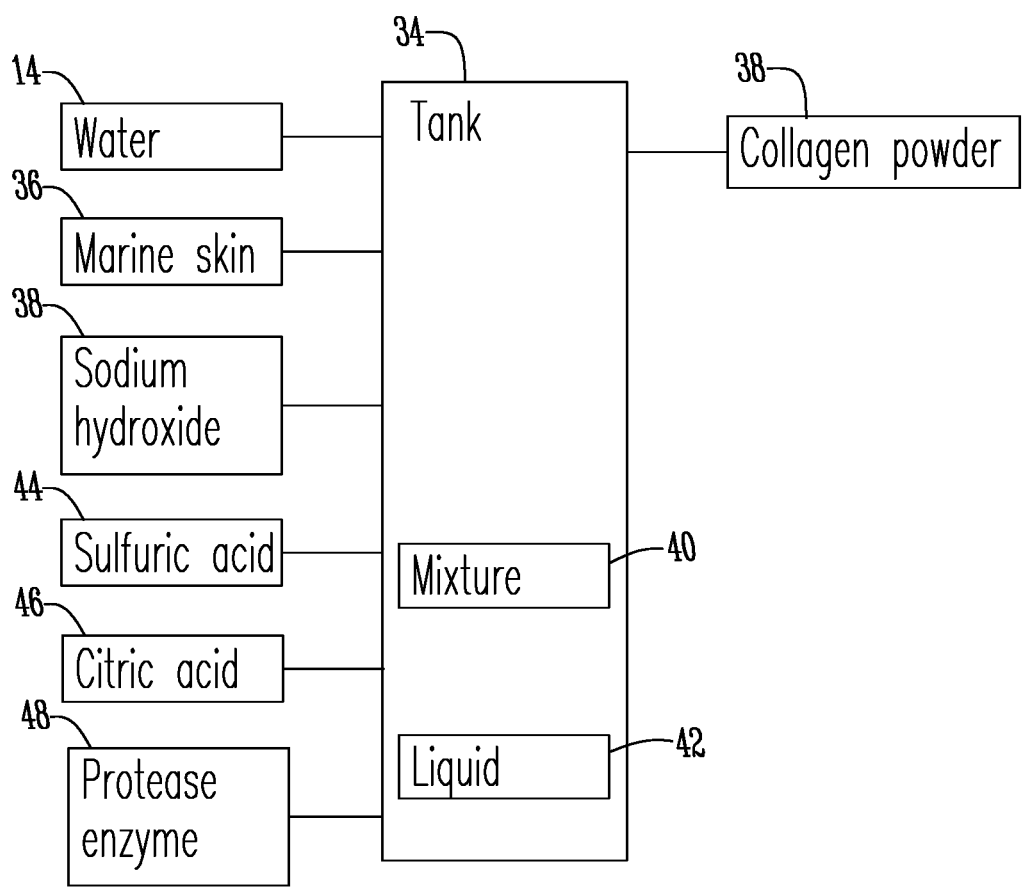
FIG. 4 is a schematic drawing of an environment for making collagen powder.

Referring to the Figures, the process of making hydrolyzed marine Type II collagen begins at step 100 by placing marine cartilage 10 into a digestion vessel or tank 12. Preferably shark cartilage in a range between 500 to 3,000 pounds is provided (and optimally 1,000 pounds of shark cartilage) to the digestion tank 12. The cartilage 10 is frozen or dried.

At step 110, between 500 and 2,500 pounds of water 14 is added to the digestion tank 12 and optimally 1,025 pounds of water 14 is added. In addition, at step 120 an enzyme 16 such as a bromalain or (ficen) is added to the digestion tank 12. Preferably, the enzyme 16 is papain in a range of 500 mLs to 20 L and optimally 4,800 mLs of 200 tyrosine units (T.U.) is added. Finally, at step 130, a neutral or alkaline protease enzyme 18 is added to the digestion tank. Preferably between 10 mLs and 20 L is added and optimally 14 L is added.

Next, at step 140, an actuator 20 in the digestion tank 12 mixes the contents while the mixture 22 is heated at a temperature of approximately 150° F. for a period of 30 minutes to 48 hours. This process turns the cartilage 10 in the mixture 22 into a liquid 26.

To deactivate the enzymes 16 and 18 after step 140, the mixture 22 is heated to a temperature of between 180° F. and 200° F. for a period of between 5 and 30 minutes at step 150. Deactivation may occur in the digestion tank 12 or the mixture 22 may be transferred to another reactor 23. Also, the deactivation step 150 may occur immediately after step 140 or after the mixture 22 has cooled at least partially.

Once the enzymes 16 and 18 are deactivated, the bone sediment 24 from the marine cartilage 10 is separated from the liquid 26 at step 160. Separation may occur by decanting, filtering, or centrifuging.

After the bone sediment 24 is separated from the liquid 26, any fat 28 in the liquid 26 is removed and/or separated from the liquid 26 in any conventional manner at step 170. Once the fat 28 is removed, the liquid 26 is transferred to a second tank 30 and heated or cooled to a temperature of between 140° F. to 170° F. at step 180.

Next, at step 190, maltodextrin 32, at a 1% to 60% weight of the mixture, is added to second tank 30 to help take away moisture from the liquid 26. Preferably, the maltodextrin 32 is added at between 30% and 32% weight. Finally, at step 200, the liquid 26 is spray dried in hot air such that the liquid evaporates and a collagen powder 33 drops and is then packaged at step 210.

Preferably, the collagen powder 33 has a molecular weight in a range between 18,000 and 180,000 Daltons. Also, preferably, the collagen powder 33 includes a minimum of 4% hyaluronic acid and typically 11%, a minimum of 5% chondroitin, between 20% and 45% of mucopolysaccharide, and a minimum of 10% protein. In one test, the collagen powder 33 included:

| Analyte | |
| --- | --- |
| Mucopolysaccharide | 43.2% |
| Hyaluronic acid | 10.71% |
| Chondroitin | 23.5% |

In addition to making the collagen powder 33, after step 160, the bone sediment 24 is dried at step 220, ground to a powder at step 230 and then packaged at step 240.

A similar method is used to make hydrolyzed marine Type I collagen. To begin, at step 300 approximately 18 L of water 14 is added to a tank or vessel 34. At step 310, marine skin 36 is added to the water 14 in the tank 34. Preferably the marine skin 36 is approximately 1,285 grams shark skin cut into squares between 0.25 and 1.5 square inches (and optimally 1 square inch). Next, at step 320, sodium hydroxide 38 is added to the tank 34 to form a mixture 40. Preferably 72 mLs of 50% sodium hydroxide 38 is added.

The mixture 40, at step 330, is then mixed for approximately 40 minutes and at step 340, the liquid 42 is drained from the skin 36. Once drained, at step 350, approximately 18 L of water 14 is added to tank 34 and mixed for 10 minutes. Once mixed, at step 360, the liquid 42 is drained from the skin 36 to wash or rinse the skin. Steps 350 and 360 are repeated preferably three times. At this point, the pH of the mixture 40 is approximately 8.0.

Next, at step 370, 18 L of water 14 is added to the tank 34. At step 380, 32 mLs of sulfuric acid 44 is added to the tank 34 and then mixed for approximately 40 minutes. When the mixing is completed, the liquid 42 is drained from the tank 34 such that the skin 36 is retained at step 390. Once drained, 18 L of water 14 and 180 grams of citric acid 46 are added to the tank 34 and mixed for approximately 40 minutes at step 400.

At step 410, again the liquid 42 is drained while retaining the skin 36. Then, at step 420, 18 L of water 14 is added to the tank 34 and mixed for about 10 minutes. Again at step 430, the liquid 42 is drained while retaining the skin 36. At this point, the pH level is between 2.8 and 3.4.

Next, at step 440, 18 L of water 14 is added to the tank 34, the mixture 40 is heated to 113° F., and the mixture 40 is mixed for about 18 hours. Upon completion, at step 450, the mixture 40 is centrifuged followed by filtering the mixture 40 at step 460 through filter pads and perlite. Once filtered, the mixture 40 is heated between 131° F. and 194° F. to evaporate the liquid 42 such that the mixture 40 is 7% to 50% solids at step 470.

Once evaporated 0.1% w/w of fungal or bacterial acid protease 48 is added to the mixture 40 at step 480 and heated at 131° F. for approximately 4 to 5 hours. Next, the mixture 40 is heated to 149° F. to deactivate the enzyme 48 at step 490. At step 500, the mixture 40 is spray dried with or without maltodextrin 32 and is packaged at step 510. The result is a Type I collagen powder 50 with less than 10% moisture and 90% to 100% protein.

The Type I collagen 50 and Type II collagen 33 powder may be blended at a 10% to 90% ratio and preferably a 50% to 50% ratio at step 520.

What is claimed is:

1. A method of making hydrolyzed marine Type I collagen, comprising the steps of:
    combining water, marine skin, and sodium hydroxide to form a mixture in a tank;
    mixing the tank for approximately 40 minutes;
    rinsing the mixture;
    adding water and sulfuric acid to the tank and mixing for approximately 40 minutes;
    draining liquid from the tank while retaining the marine skin;
    adding citric acid and water to the tank and mixing for approximately 40 minutes; and
    draining the citric acid and water, and thereafter adding water and draining the water until the pH of the mixture is between 2.8 and 3.4.

2. The method of claim 1 further requiring the step of filtering and evaporating the mixture until the mixture is between 7% and 50% solid.

3. The method of claim 2 further requiring the step of adding an acid protease to the mixture.

4. A method of making hydrolyzed marine Type I collagen, comprising the steps of:
    combining water, marine skin, and sodium hydroxide to form a mixture in a tank;
    mixing, draining, and refilling the tank to bring the pH of the mixture to approximately 8.0;
    adding water and sulfuric acid to the tank and mixing;
    draining the liquid from the tank while retaining the marine skin;
    adding citric acid and water to the tank and mixing; and
    draining the citric acid and water; and
    adding water and draining the tank until the pH of the mixture is between 2.8 and 3.4.

5. The method of claim 4 further comprising the steps of adding water to the tank, heating the mixture to 113° F., and mixing the mixture for approximately 18 hours.

6. The method of claim 5 further comprising the step of centrifuging the mixture followed by filtering the mixture through filter pads and perlite.

7. The method of claim 6 further comprising the step of heating the mixture after filtering to between 131 and 194° F. to evaporate liquid leaving a mixture that is 7 to 50% solid.

8. The method of claim 7 further comprising the step of adding an acid protease to the mixture and heating the mixture at 131° F. for between 4 and 5 hours.

9. The method of claim 8 further comprising the step of heating the mixture to 149° F. to deactivate the enzyme.

10. The method of claim 9 further comprising the step of adding maltodextrin to the mixture and spraying the mixture dry.

11. A method of making hydrolyzed marine Type I collagen, comprising the steps of:
    a. combining water, marine skin, and sodium hydroxide to form a mixture in a tank;
    b. mixing, draining, and refilling the tank to bring the pH of the mixture to approximately 8.0;
    c. adding water and sulfuric acid to the tank and mixing;
    d. draining the liquid from the tank while retaining the marine skin;
    e. adding citric acid and water to the tank and mixing;
    f. draining the citric acid and water;
    g. adding water and draining the tank until the pH of the mixture is between 2.8 and 3.4;
    h. adding water to the tank, heating the mixture to 113° F., and mixing the mixture for approximately 18 hours;
    i. centrifuging the mixture followed by filtering the mixture through filter pads and perlite;
    j. heating the mixture after filtering to between 131 and 194° F. to evaporate liquid leaving a mixture that is 7 to 50% solid;
    k. adding an acid protease to the mixture and heating the mixture at 131° F. for between 4 and 5 hours;

l. heating the mixture to 149° F. to deactivate the enzyme; and m. adding maltodextrin to the mixture and spraying the mixture dry;

wherein steps a-m are completed in sequence.

12. The method of claim 11 wherein step b. is repeated three times.

\* \* \* \* \*